(12) United States Patent
Kight (10) Patent No.: US 9,005,149 B1
(45) Date of Patent: Apr. 14, 2015

(54) SPINAL DECOMPRESSION AND SLEEP THERAPY SYSTEM

(71) Applicant: John A. Kight, Morrisville, NC (US)

(72) Inventor: John A. Kight, Morrisville, NC (US)

(73) Assignee: STUD Medical Ltd., Tortola (VG)

( * ) Notice: Subject to any disclaimer, the term of this patent is extended or adjusted under 35 U.S.C. 154(b) by 0 days.

(21) Appl. No.: 14/276,900

(22) Filed: May 13, 2014

Related U.S. Application Data (63) Continuation-in-part of application No. 14/183,390, filed on Feb. 18, 2014.

(60) Provisional application No. 61/892,948, filed on Oct. 18, 2013.

(51) Int. Cl.
*A61F 5/02* (2006.01)
*A61F 5/055* (2006.01)
*A61F 5/058* (2006.01)

(52) U.S. Cl.
CPC ............... *A61F 5/026* (2013.01); *A61F 5/028* (2013.01); *A61F 5/055* (2013.01); *A61F 5/05883* (2013.01)

(58) Field of Classification Search
CPC ..... A61F 5/026; A61F 5/3707; A61F 5/3715; A61F 5/055; A61F 5/05883; A61F 5/028
USPC ................ 602/17–19, 36, 40; 128/98.1, 99.1, 128/100.1, 101.1, 874–876, 869, 845–846; 119/857; 2/44–45, 308–310; 482/91, 482/124–125, 131, 907, 121, 122; 601/33
See application file for complete search history.

(56) References Cited

U.S. PATENT DOCUMENTS

| | | | | |
|---|---|---|---|---|
| 880,904 | A | * | 3/1908 | Mueller ................................ 2/44 |
| 1,301,276 | A | * | 4/1919 | Kroetz ............................. 602/19 |
| 2,973,939 | A | | 2/1961 | Matthewson |
| 3,176,793 | A | * | 4/1965 | Hlacia ................................ 182/3 |
| 4,570,619 | A | * | 2/1986 | Gamm ............................. 602/19 |
| 4,609,193 | A | | 9/1986 | Paris et al. |
| 4,700,697 | A | | 10/1987 | Mundell |
| 4,777,678 | A | | 10/1988 | Moore |
| 4,876,755 | A | | 10/1989 | Parrish |
| 5,027,833 | A | * | 7/1991 | Calkin ........................... 128/870 |
| 5,063,625 | A | | 11/1991 | Perry |
| 5,774,916 | A | | 7/1998 | Kurhi |
| 5,816,251 | A | * | 10/1998 | Glisan ........................... 128/845 |
| 5,893,365 | A | * | 4/1999 | Anderson ..................... 128/848 |
| 5,987,675 | A | | 11/1999 | Kim |
| 6,182,311 | B1 | | 2/2001 | Buchanan et al. |
| 6,190,342 | B1 | * | 2/2001 | Taylor ............................. 602/19 |
| 6,289,893 | B1 | | 9/2001 | Levitt |
| 6,357,444 | B1 | | 3/2002 | Parker |

(Continued)

*Primary Examiner* — Victoria J Hicks
*Assistant Examiner* — Kari Petrik (57) ABSTRACT

The present invention relates generally to a home therapy system for aiding spinal cord decompression and for treating related health issues. More specifically, the present invention teaches a garment system combining an upper portion and lower portion. According to a preferred embodiment, the upper portion includes a head band and yoke for cervical vertebra disc decompression and for aiding in treating Obstructive Sleep Apnea by repositioning and opening up breathing airways. Further in accordance with a preferred embodiment, the lower portion includes vertical decompression straps attached to leg bands and extending over the shoulders for thoracic and lumbar disc decompression by arching the spinal column back and opening the vertebra.

6 Claims, 6 Drawing Sheets

(56) References Cited

U.S. PATENT DOCUMENTS

| | | |
|---|---|---|
| 6,615,832 B1 | 9/2003 | Chen |
| 6,671,906 B1 | 1/2004 | Milligan |
| 6,671,907 B1 | 1/2004 | Zuberi |
| 6,698,432 B2 | 3/2004 | Ek |
| 6,751,818 B2 | 6/2004 | Troop |
| 6,921,375 B2 | 7/2005 | Kihara |
| 6,926,008 B1 | 8/2005 | Levitt |
| 7,134,435 B2 | 11/2006 | Scott |
| 7,546,651 B2 | 6/2009 | Groteke et al. |
| 7,703,849 B2 | 4/2010 | Bilak et al. |
| 7,725,195 B2 | 5/2010 | Lima et al. |
| 7,743,768 B2 | 6/2010 | Ho et al. |
| 8,037,562 B2 | 10/2011 | Kemper et al. |
| 8,118,030 B1 | 2/2012 | Bugeja |
| 8,234,732 B2 | 8/2012 | Bacon |
| 8,449,486 B2 | 5/2013 | Gomez, Jr. et al. |
| 8,795,213 B2 * | 8/2014 | Mills .............................. 602/19 |
| 2005/0028240 A1 | 2/2005 | Brennan |
| 2007/0131231 A1 * | 6/2007 | Sharp ........................... 128/848 |
| 2008/0156332 A1 | 7/2008 | Charles |
| 2011/0100375 A1 | 5/2011 | Tannahill et al. |
| 2011/0137343 A1 | 6/2011 | Vitko |
| 2013/0014766 A1 | 1/2013 | Crocetti |
| 2013/0104279 A1 | 5/2013 | Galli, Jr. et al. |
| 2013/0191965 A1 | 8/2013 | Edwards |
| 2013/0205471 A1 | 8/2013 | Alvarez |

* cited by examiner

Point of Adjustment

Point Of Attachment

Point of Adjustment
Point Of Attachment

SPINAL DECOMPRESSION AND SLEEP THERAPY SYSTEM

CROSS-REFERENCE TO RELATED APPLICATION

This application is a Continuation-In-Part and claims the benefit of U.S. application Ser. No. 14/183,390 entitled "SPINAL DECOMPRESSION AND SLEEP THERAPY SYSTEM" filed Feb. 18, 2014 which is incorporated by reference herein.

BACKGROUND OF THE INVENTION

1. Field of Invention

The present invention relates generally to a home therapy system for aiding spinal cord decompression and in particular, to a garment system combining an upper portion having a head band and yoke for cervical vertebra disc decompression; and a lower portion having vertical decompression straps attached to leg bands and extending over the shoulders for thoracic and lumbar disc decompression.

2. Description of the Prior Art

The human body is designed to stand vertically upright, with the chin up slightly and the head positioned forward angled toward the horizon. Today, the common use of electronics forces users to spend hours every day looking down and thereby exerting damaging pressure on the C1 through C7 anterior cervical vertebra discs causing disc degeneration. The head weighs 8 to 12 pounds and for every centimeter the head is tilted forward there is a substantial increase in damaging pressure on the anterior cervical disc, resulting in nerve blockage over time.

When a disc degenerates, its ability to resist loads and pressure is greatly compromised and the peripheral nerves leading from the spinal column are affected. The affected areas supported by these peripheral nerves will become denervated over time and lose their intended functions as the disc become flatter causing increased damage to the peripheral nerves. This situation could cause pain, tingling or numbness in the affected areas, or if the affected area is the Pharynx, loose obstructive tissue, or double chins with a chicken neck appearance. The peripheral nervous system allows for the brain to direct and control every chemical reaction in every cell in the body so when these nerves are pinched, stretched or inflamed due to damaged disc the affected areas are compromised from their optimal functionality sometimes causing symptomatic diseases we experience today. The decompression of the entire spinal column allows the brain to send and receive the nerve impulses required for healing of the body's organs, systems, bones, tendons, ligaments and muscles. Home spinal decompression devices have been proposed for various uses, such as those disclosed in U.S. Pat. No. 8,083,705 to Saunders et al. in which a pneumatic traction force is generated by a hand pump operated by the patient. This apparatus is expensive, bulky, inconvenient and not wholly restorative.

U.S. Pat. No. 8,079,971 to Becerra discloses a spinal mobilization treatment system with multi-dimensional force application. Similar to the device of Saunders et al., the patient lies upright on this apparatus and a harness and cable are attached to a computer device which applies forces at different angles.

As with Saunders et al. and Becerra, U.S. Pat. No. 8,021,287 to Hoffman et al. also consists of harnessing the patient to a device in which forces are applied using traction in order to reposition the spine in a pain-free position for performing exercises. The apparatus of Hoffman may be useful in a physical therapy setting for acute back pain suffers but it offers no long term passive mode of restoration to the spine and nervous system. Further, it fails to promote the natural tendency of the body to heal itself during periods of sleep.

U.S. Pat. No. 8,011,047 to Mandelzis et al. teaches a design to promote a good sleeping position by passively distributing body mass and muscle tension forces in a unidirectional fashion. This design includes a spinal length mattress made of memory foam. While this design may provide a certain degree of comfort while sleeping, it is limited in its therapeutic benefits. Further, the foam mattress of Mandelzis is bulky and relatively costly.

Other traction devices such as U.S. Pat. No. 7,270,628 to Campanaro et al., U.S. Pat. No. 6,997,892 to Reinecke and U.S. Pat. No. 6,974,432 to Reinecke et al. also employ pulleys or cables, support belts, lifting mechanisms and digital devices for applying pressure to manipulate a patient's spine into proper alignment. Each of the designs presents complicated mechanisms for applying unnatural forces to a patient's torso during specific periods of exercise or therapy in which treatment must be monitored. Together, these devices, along with all related prior art, simply fail to provide the relief and healing of the present invention.

SUMMARY OF INVENTION

According to embodiments of the present invention, a non-chemical, non-invasive, lightweight, portable system and apparatus to promote natural healing is provided. More specifically, the spinal vertebra disc decompression, exercise and sleep therapy apparatus of the present invention provides therapy to reduce or eliminate pain and discomfort caused by pinched nerves while increasing health, energy, stamina and alertness.

According to a first preferred embodiment, the present invention has an upper portion and a lower portion. Preferably, the upper portion includes a light weight elastic head band, a light weight yoke to gently pull the shoulders back, and vertical decompression straps stretched between the head band and the yoke strap to gently pull the head back. The lower portion includes leg bands around the upper thighs of the wearer and vertical decompression straps attached to the leg bands. For the lower portion, each vertical decompression strap preferably attaches between a single leg band by extending up from the outer thigh region of the leg band and running across the back of the wearer, over the opposite shoulder and then running under the arm and back across the back of the wearer to attach to the outer thigh region of the same leg band. By crisscrossing the straps across the body, a four strap system is created which manipulates the thoracic and lumbar spinal column by gently pulling the spinal column back, opening up the spinal column. This apparatus preferably weighs less than one pound and can be easily stored, transported and assembled.

One advantage of the present invention is that it repositions and opens the airways of the wearer decreasing obstruction in the airway which causes snoring and Obstructive Sleep Apnea allowing for increased oxygen intake. Still further, the present invention allows for the strengthening of the neck muscles and tendons and helps improve the appearance of the chin and neck by firming the muscles and tendons in the neck.

These and other aspects of the invention will become apparent from the following description of the preferred embodiments taken in conjunction with the following drawings. As would be obvious to one skilled in the art, many variations and modifications of the invention may be made without departing from the spirit and scope of the novel concepts of the disclosure.

DETAILED DESCRIPTION OF THE INVENTION

The figures and descriptions which follow serve to explain in greater detail the many aspects of the various preferred embodiments of the present invention. Referring to the drawings, like numbers indicate like parts through the views. Unless otherwise specifically indicated in the disclosure that follows, the drawings are not necessarily drawn to scale. As used in the description herein and through the claims, the following terms take the meanings explicitly associated herein, unless the context clearly dictates otherwise: the meaning of "a," "an," and "the" includes plural reference. The meaning "in" includes "in" and "on."

Figure 1:
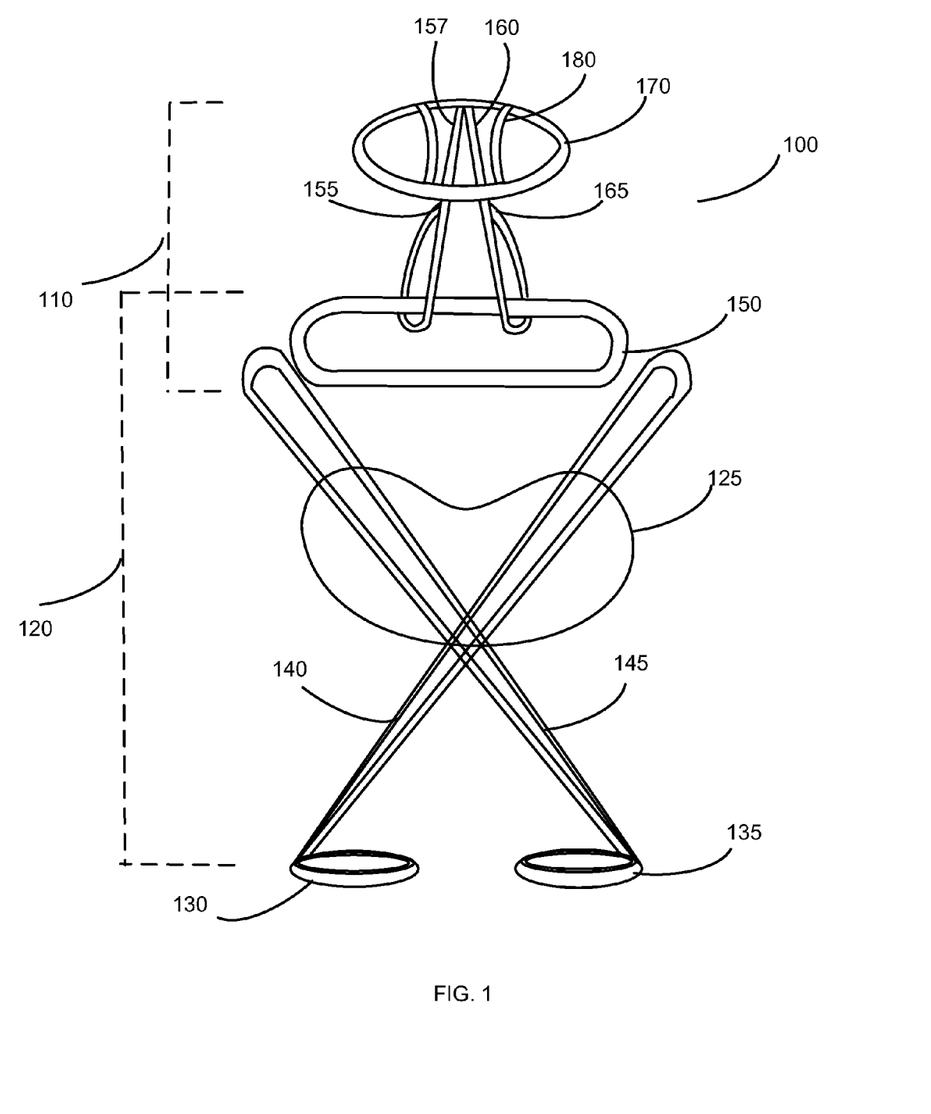
FIG. 1 shows an exemplary embodiment of the present invention.

With reference now to FIG. 1, an exemplary embodiment of the present invention will now be discussed. As shown in FIG. 1, the spinal decompression and sleep therapy system 100 of the present invention includes an upper portion 110 and a lower portion 120. Preferably, the upper portion 110 contains a head band 170, vertical decompression straps 157, 160 and a yoke 150. The head band 170 preferably includes suspension straps 180 which function to keep the head band 170 in place. Alternatively, the head band 170 may function without the use of the suspension straps 180.

Preferably, the vertical decompression straps 157, 160 attach to the back of the head band 170 and extend down the neck of the wearer to attach to the back of the yoke 150. As discussed below with respect to FIG. 6B, according to a preferred embodiment, the vertical decompression straps 157, 160 are preferably attached to the lower yoke portion (shown as portion 640 in FIG. 6B) which runs across the back of the wearer. Alternatively, as shown in FIG. 5B, the vertical decompression straps 157, 160 may attach to the upper yoke portion (shown as portion 560P in FIG. 5B).

As shown in FIG. 1, the vertical decompression straps 157, 160 may preferably further include adjustable attachment points 155, 165 to allow for changes in the length of the vertical decompression straps 157, 160. The yoke 150 is preferably a circular elastic strap which goes from around the back of the neck, crossing over the front of the shoulders, under the arms and across the back allowing the tension to hold the shoulders back.

As further shown in FIG. 1, the lower portion 120 of the present invention preferably includes two vertical decompression straps 140, 145 extending from each of two leg bands 130, 135. According to a preferred embodiment, each vertical decompression strap 140, 145 preferably attaches to a leg band and extends up from each leg band, over the opposite shoulder, back under the arm and across the back of the wearer to attach to the same leg band. Ideally, the starting and end points for each strap will be approximately ⅛ of the leg band circumference to the outside of the thigh or 45 degrees toward the outside of the center back of the thigh allowing for the vertical decompression straps to cross over the glutes.

As specifically shown in FIG. 1, vertical decompression strap 140 preferably attaches to the outside portion of leg band 130 and then runs over the opposite shoulder, back under the arm and across the back of the wearer to attach back to the outside portion of leg band 130. Conversely, vertical decompression strap 145 preferably attaches to the outside portion of leg band 135 and then runs over the opposite shoulder, back under the arm and across the back of the wearer to attach back to the outside portion of leg band 135. Within the concept of the present invention, one or more additional straps may be used to add additional tension and support. In use, a system of four or more crisscrossed straps is preferably created which manipulates the thoracic and lumbar spinal column by gently pulling the spinal column back, opening up the spinal column.

According to a preferred embodiment, the decompression straps preferably cross as shown in FIG. 1. Alternatively, the decompression straps may attach to the outside portion of a leg band and then run over the same shoulder and back down to the outside portion of the same leg band. In this configuration, the decompression straps run parallel to each other.

As shown, the vertical decompression straps 140, 145 of the lower portion are not attached to the yoke 150 of the upper portion. However, according to an alternative embodiment, the vertical decompression straps 140, 145 may be attached to the yoke 150 if desired. Further, the decompression straps 140, 145 may alternatively be attached directly to each other (i.e. where they crisscross) to assist in maintaining their relative positions when in use. In accordance with a further preferred embodiment, a decompression support pillow 125 may be inserted beneath the system of crisscrossed straps for assisting back sleepers. This decompression support pillow may preferably be attached with a belt to further secure it to the body when sleeping.

Figure 2:
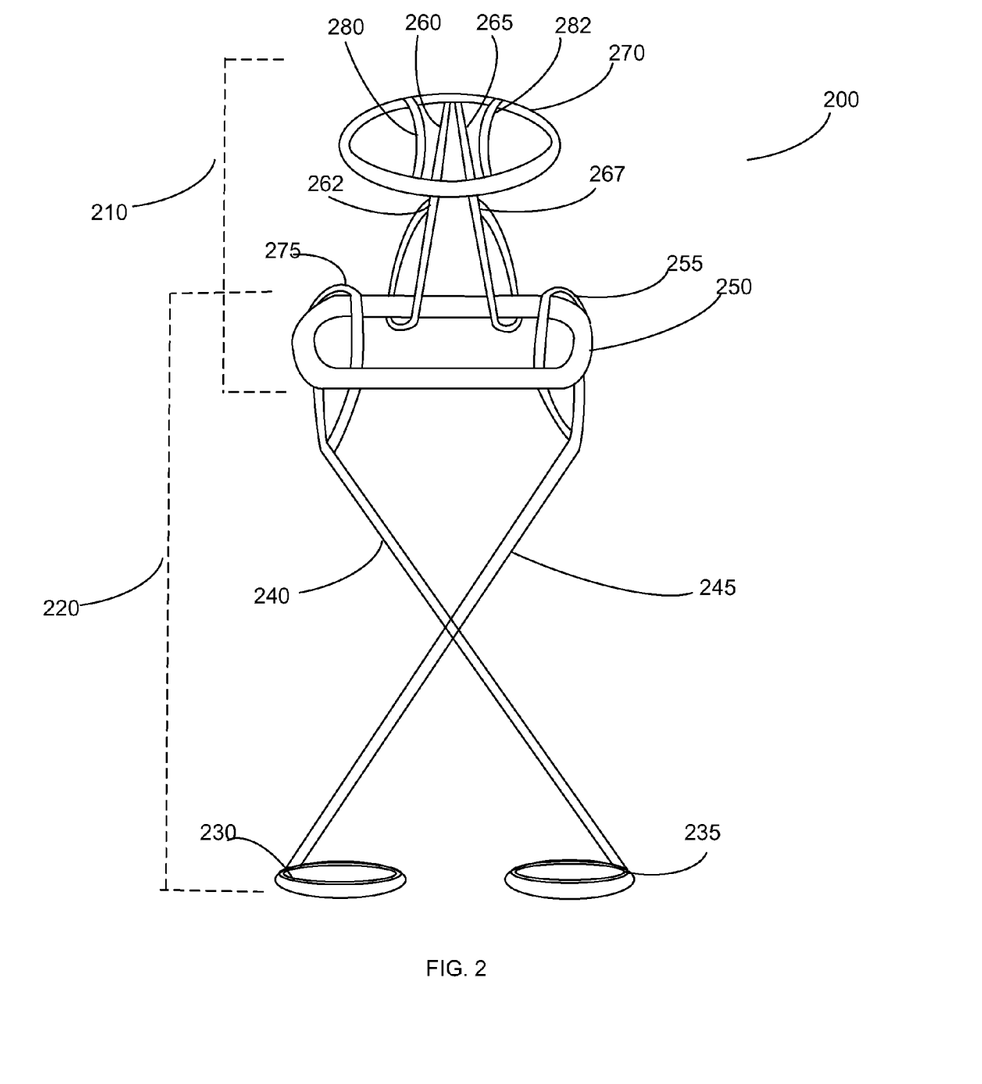
FIG. 2 shows an alternative embodiment of the present invention.

With reference now to FIG. 2, an alternative embodiment of the present invention will now be further discussed. As shown in FIG. 2, the system 200 of the present invention includes the same upper 210 and lower 220 portions described in FIG. 1. As shown, the upper portion 210 may preferably include a head band 270, vertical decompression straps 260, 265 and a yoke 250. The head band 270 preferably includes suspension straps 280, 282 which function to keep the head band 270 in place. The vertical decompression straps 260, 265 preferably attach to the back of the head band 270 and extend down the neck of the wearer to attach to the back of the yoke 250. The vertical decompression straps 260, 265 may further include adjustment points 262, 267 to allow for changes in the length of the vertical decompression straps 260, 265. The lower portion 220 as shown includes each of the two leg bands 230, 235 attached to vertical decompression elastic straps 240, 245 which crisscross and attach to opposite corners 255, 275 of the yoke 250. More specifically, vertical decompression strap 245 is shown attached to leg band 230 and crossing the back of the wearer to attach to the opposite corner 255 of the yoke 250. Conversely, vertical decompression strap 240 is shown attached to leg band 235 and crossing the back of the wearer to attach to the opposite corner 275 of the yoke 250. In this embodiment, the adjustment of the vertical decompression straps may preferably be just below the yoke and the shoulder blades if the wearer is smaller framed.

Figure 3:
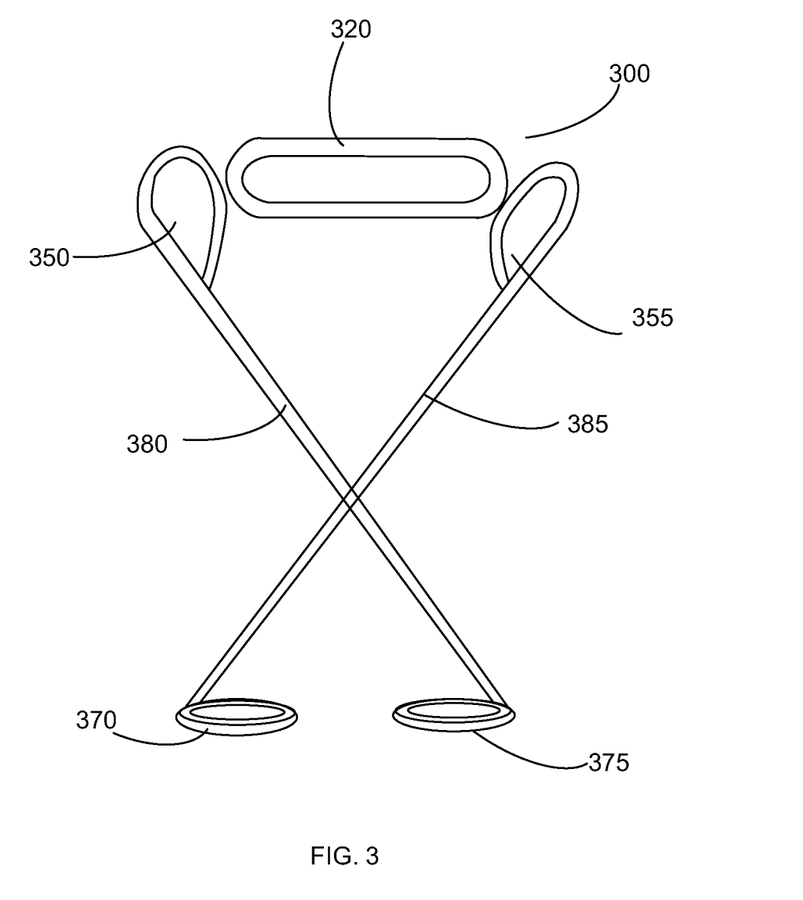
FIG. 3 shows example attachment and adjustment points for an exemplary embodiment of the present invention.

With reference now to FIG. 3, a second alternative embodiment of the present invention will now be further discussed. As shown in FIG. 3, the lower portion 300 preferably includes two leg bands 370, 375 each attached to vertical decompression bands 380, 385 which crisscross and attach to opposite shoulders of the wearer via arm holes 350 and 355. More specifically, vertical decompression strap 385 is shown attached to leg band 370 and crossing the back of the wearer to attach to the opposite shoulder of the wearer via arm hole 355. Conversely, vertical decompression strap 380 is shown attached to leg band 375 and crossing the back of the wearer to attach to the opposite shoulder of the wearer via arm hole 350. In use, the vertical decompression straps 380, 385 preferably cross in the back and pull each shoulder with enough tension to gently roll the shoulders back and open the chest thus allowing the vertebra to open up alleviating pressure and decompressing the thoracic and lumbar portions of the spinal vertebra.

Preferably, the tension maintained by the each vertical decompression strap should start out to provide a comfortable and gentle arch in the neck, thoracic and lumbar areas when at rest or asleep. Over time, as the muscles and tendons adjust to the decompression therapy device, the device can gradually be adjusted tighter to offer a firmer decompression arch allowing the muscles and tendons to adjust to the therapy. If the wearer experiences any soreness or discomfort from the therapy, the resistance may then be decreased.

Figure 4:
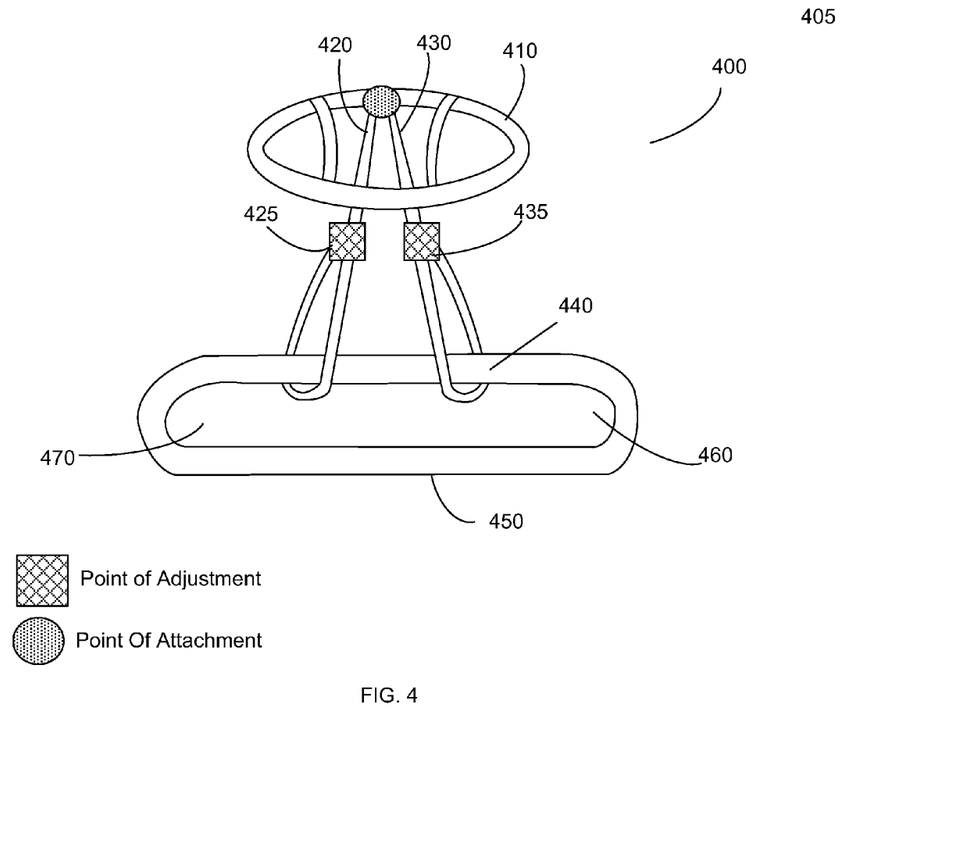
FIG. 4 shows example attachment and adjustment points for an exemplary upper portion of an embodiment of the present invention.

With reference now to FIG. 4, an exemplary assembly of the upper portion 400 of the present invention will now be discussed. As shown in FIG. 4, the head band 410 may be attached to the back section of the yoke 440 by one or more vertical decompression straps 420, 430 leading from the back side of the headband 410 to the yoke 440. Preferably, the yoke 440 is designed to hold the shoulders back and anchor the cervical decompression straps. The vertical decompression straps 420, 430 may further include adjustable attachment points 425, 435 to allow for changes in the length of the vertical decompression straps 420, 430. According to a preferred embodiment, the head band 410 is preferably worn to allow the vertical decompression straps 420, 430 attached on the back side to be tight enough to gently pull the head back when neck muscles are relaxed but not so tight to cause discomfort or injury. As discussed below with respect to FIG. 6B, according to a preferred embodiment, the vertical decompression straps 420, 430 are preferably attached to the lower yoke portion (shown as portion 640 in FIG. 6B) which runs across the back of the wearer. Alternatively, as shown in FIG. 5B, the vertical decompression straps 420, 430 may attach to the upper yoke portion running behind the neck of the wearer (shown as portion 560P in FIG. 5B).

Figure 5A:
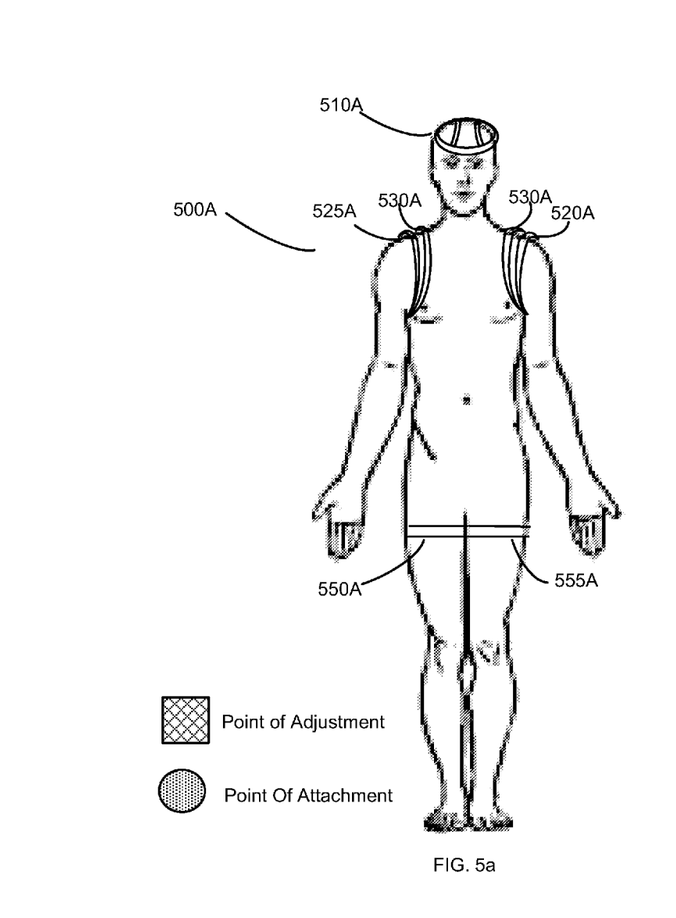
FIG. 5a shows an anterior illustration of a figure wearing an exemplary embodiment of the present invention.
Figure 5B:
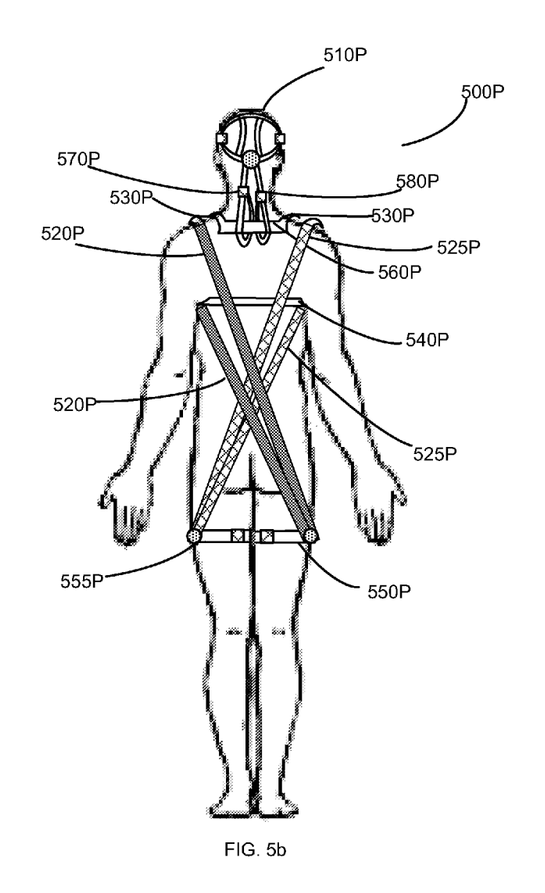
FIG. 5b shows a posterior view of a figure wearing an exemplary embodiment of the present invention.

With reference now to FIG. 5a, an anterior illustration of a figure wearing an apparatus in accordance with the present invention will now be discussed. As shown in FIG. 5a, yoke 530A is preferably worn to run behind the neck, over the anterior shoulders, under the armpits and around the back of the wearer. Preferably, the yoke 530A is formed of a neoprene elastic material (or any alternative material with similar elasticity properties) from the sides of the chest to the center of the back which would allow for the shoulders to be gently pulled back during rest or sleep.

FIG. 5a provides an anterior view of one embodiment of the present invention which shows the headgear 510A, the front portion of the leg bands 550A, 555A and a portion of the vertical decompression straps 520A, 525A.

With reference now to FIG. 5b, a posterior view of a figure wearing an apparatus in accordance with the present invention will now be discussed. As shown in FIG. 5b, the headgear 510P preferably fits as a headband with the decompression straps 570P, 580P stretched vertically from the back of the head gear 510P to the center of the back of the upper portion of the elastic yoke strap 560P. Preferably, there should be enough tension to hold the head back with relaxed neck muscles, which will gently pull the head back while at rest or in a state of sleep.

As further shown in FIG. 5b, there are preferably two adjustable leg bands 550P, 555P worn on the upper thigh with vertical decompression straps 520P, 525P extending over opposite shoulders and attaching back to each leg band 550P, 555P. Preferably, the attachment points for each leg band will be approximately ⅛ of the leg band circumference toward the outside of the thigh or at a location to create an angle of assent for the path of each strap between the leg band attachment point and the opposite shoulder. More specifically as shown in FIG. 5b, in accordance with a preferred embodiment, vertical decompression strap 520P attaches to leg band 550P on the outside of the thigh and extends up and over the opposite shoulder and back down under the arm to attach back to leg band 550P. Conversely, vertical decompression strap 525P attaches to leg band 555P on the outside of the thigh and extends up and over the opposite shoulder and back down under the arm to attach back to leg band 555P.

As further shown in FIG. 5b, various points of adjustment and attachment may be seen. However, it should be appreciated that the system of the present invention may be structured to provide more or fewer attachment points and adjustment points as needed. For instance, the vertical decompression straps may attach to each other and/or at other specifically selected point(s) of adjustment for a particular wearer.

Figure 6A:
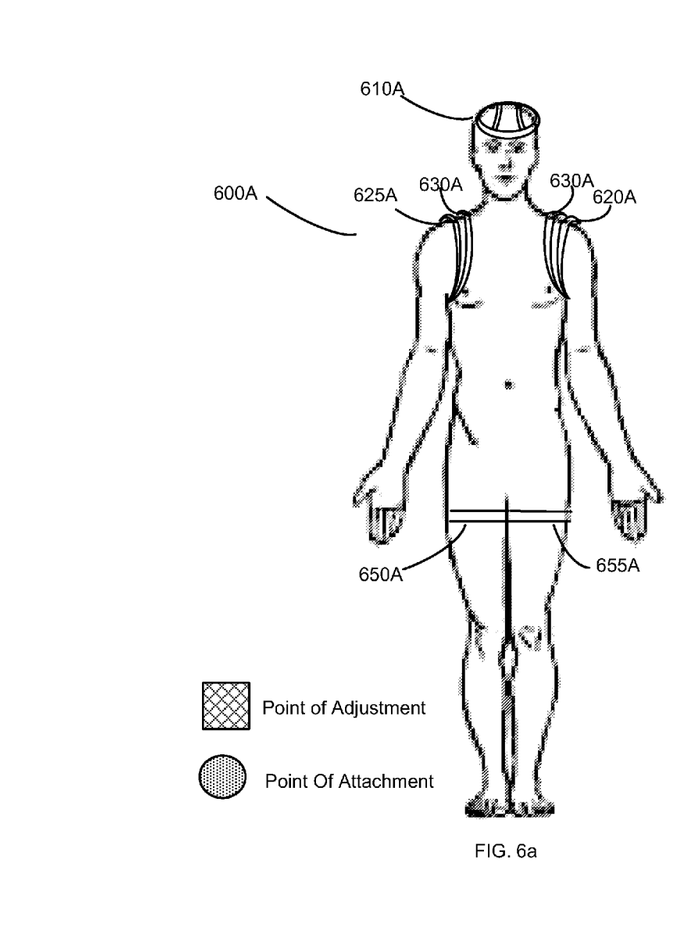
FIG. 6a shows an anterior illustration of a figure wearing an exemplary embodiment of the present invention.

With reference now to FIG. 6a, an anterior view of a figure wearing an apparatus in accordance with the present invention will now be discussed. As shown in FIG. 6a, the circular elastic yoke 630A may be worn behind the neck around and under the anterior shoulders and armpits and around the back. This yoke band 630A may be neoprene elastic material (or any alternative material with similar elasticity properties) from the sides of the chest to the center of the back which would allow for the shoulders to be gently pulled back during rest or sleep. As further shown in FIG. 6a, an anterior view of the headgear 610A, the front portion of the leg bands 650A, 655A and a portion of the vertical decompression straps 620A, 625A is provided.

Figure 6B:
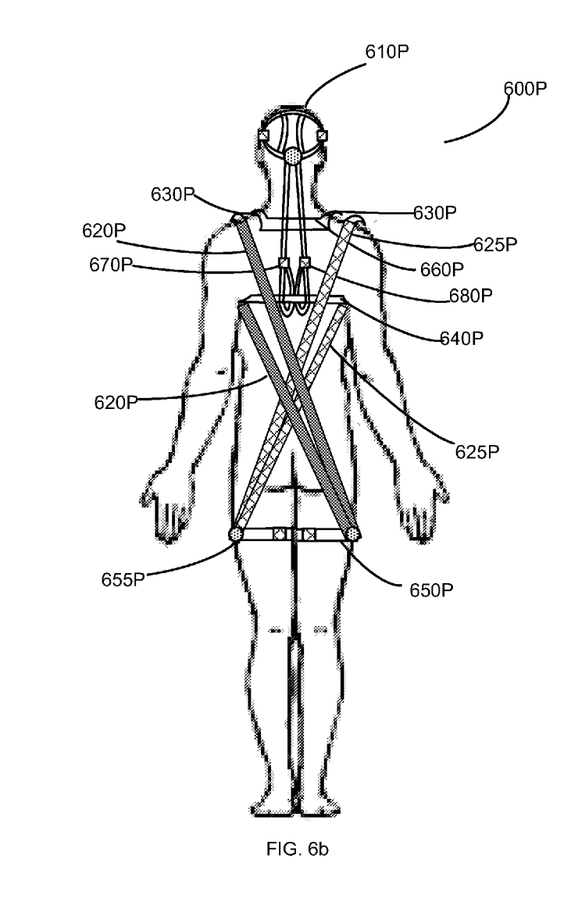
FIG. 6b shows a posterior view of a figure wearing an exemplary embodiment of the present invention.

With reference now to FIG. 6b, a posterior view of a figure wearing an apparatus in accordance with the present invention will now be discussed. As shown in FIG. 6b, the headgear 610P preferably fits as a headband with the decompression straps 670P, 680P stretched vertically from the back of the head gear 610P to the center of the back of the lower portion the elastic yoke strap 640P. Preferably, there should be enough tension to hold the head back with relaxed neck muscles, which will gently pull the head back while at rest or in a state of sleep. As further shown in FIG. 6b, there are preferably two adjustable leg bands 650P, 655P worn on the upper thigh with vertical decompression straps 620P, 625P extending over opposite shoulders and attaching back to each leg band 650P, 655P. Preferably, the attachment points for each leg band will be approximately ⅛ of the leg band circumference toward the outside of the thigh or at a location to create an angle of assent for the path of each strap between the leg band attachment point and the opposite shoulder.

More specifically as shown in FIG. 6b, in accordance with a preferred embodiment, vertical decompression strap 620P attaches to leg band 650P on the outside of the thigh and extends up and over the opposite shoulder and back down under the arm to attach back to leg band 650P. Conversely, vertical decompression strap 625P attaches to leg band 655P on the outside of the thigh and extends up and over the opposite shoulder and back down under the arm to attach back to leg band 655P.

There may be multiple variations in the positioning of the vertical decompression straps in both the upper and lower portions of the disc decompression system of the present invention. For example, both straps may be crisscrossing (as shown) or both straps may be positioned straight up and down such that the strap that stretches across the right shoulder attaches to the right leg band and the strap that stretches across the left shoulder attaches to the left leg band. Another possible configuration of the vertical decompression straps may be that one strap is slanting diagonally across the back of the body around one shoulder and extending to the opposite leg band; while a second strap is stretched straight up and down around the other shoulder and attaches to the same leg band. It may also be preferable depending on the size of the wearer, that the wearer uses more than two vertical decompression straps and adjusts the angle of each strap differently relative to shoulders and the outer edge of at least one of the leg bands.

Properly adjusted, the disc decompression system of the present invention will ideally provide gentle resistance causing pulling or arching of the spinal column back while in a relaxed sleep state allowing the spinal disc to decompress and heal while asleep. This system may also be worn under clothes to offer posture support and decompression while performing daily activities.

According to a preferred embodiment, adjustment of the straps may be provided by hook and loop material (e.g. Velcro), elastic, press studs etc. Alternatively, the attachment assembly may include buckle assemblies. The following is a list of some exemplary types of attachments and releases that may be considered durable for use in the system of the present invention: Velcro one-wrap strap, Velcro nylon straps with buckle, Velcro buckle, durable Velcro strap buckle, Velcro cable tie metal buckle, Velcro buckle strap with back to back, adhesive Velcro buckle, Velcro buckle, die-cut sticky Velcro buckle, hook and loop Velcro buckle strap, hook and loop cable tie/Velcro, Velcro buckle/hook and loop cable tie, Velcro buckle straps, adjustable elastic Velcro buckle strap, and strap buckle Velcro.

According to one embodiment of the present invention and to assist in healing while asleep, there may be an elastic material or neoprene chin strap which could be used to gently hold the bottom jaw closed to encourage breathing through the nose (the nose and sinus system offers the ideal heat and moisture exchange system). The chin strap may also serve to support the head band.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A spinal decompression and sleep therapy system, the system comprising:
    a cervical decompression device comprising:
        a head band;
        a yoke, wherein the yoke is a circular elastic band configured to be worn around a back of a wearer, over a front of the wearer's shoulders and behind a neck of the wearer to pull the shoulders of the wearer back; and
        at least one vertical decompression neck strap, wherein the vertical decompression neck strap is attached at one point to the head band and at another point to the yoke so as to exert tension between the vertical decompression neck strap and the yoke; and
    a thoracic and lumbar decompression device comprising:
        a first leg band configured to secure to a first thigh of the wearer;
        a second leg band configured to secure to a second thigh of the wearer;
        a first vertical decompression leg strap, wherein the first vertical decompression leg strap is configured to extend from the first leg band, diagonally across the back of the wearer, over the opposite shoulder of the wearer and back to the first leg band of the wearer;
        a second vertical decompression leg strap, wherein the second vertical decompression leg strap is configured to extend from the second leg band, diagonally across the back of the wearer, over the opposite shoulder of the wearer and back to the second leg band of the wearer.

2. The spinal decompression and sleep therapy system of claim 1, wherein a starting point and an ending point for each vertical decompression leg strap is approximately ⅛ of the leg band circumference toward an outside of the thigh.

3. The spinal decompression and sleep therapy system of claim 1, further comprising a chin strap configured to hold the bottom jaw of the wearer closed during use.

4. The spinal decompression and sleep therapy system of claim 1, wherein the vertical decompression leg straps of the thoracic and lumbar decompression device are attached directly to each other to assist in maintaining their relative positions when in use.

5. The spinal decompression and sleep therapy system of claim 1, wherein the system further comprises a decompression support pillow.

6. The spinal decompression and sleep therapy system of claim 5, wherein the system further comprises a belt for attaching the decompression support pillow to the wearer.

* * * * *